US00PP28510P2

(12) United States Plant Patent
Lannes

(10) Patent No.: US PP28,510 P2
(45) Date of Patent: Oct. 10, 2017

(54) ***HIBISCUS* PLANT NAMED 'LANOUACHITA'**

(50) Latin Name: *Hibiscus rosa-sinensis*
Varietal Denomination: Lanouachita

(71) Applicant: Robert M. Lannes, Malause (FR)

(72) Inventor: Robert M. Lannes, Malause (FR)

(73) Assignee: D.H.M INNOVATION, Malause (FR)

( * ) Notice: Subject to any disclaimer, the term of this patent is extended or adjusted under 35 U.S.C. 154(b) by 0 days.

(21) Appl. No.: 15/330,113

(22) Filed: Aug. 9, 2016

(51) Int. Cl.
*A01H 5/02* (2006.01)

(52) U.S. Cl.
USPC ..... Plt./257

(58) Field of Classification Search
USPC ..... Plt./257
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Hibiscus* named 'Lanouachita' that is characterized by its flowers that are mottled tangerine orange in color with pink highlights and center, its floriferous habit with flowers that last for 2 to 3 days, its early blooming and freely flowering habit, its moderately upright, compact and self-branching plant habit, and its foliage that is resistant to pathogens common to *Hibiscus*, including *Pseudomonas* sp., *Phythium* sp., and *Phytophthora* sp.

2 Drawing Sheets

Botanical classification: *Hibiscus rosa-sinensis.*
Cultivar designation: 'Lanouachita'.

BACKGROUND OF THE INVENTION

The present invention relates to a new and distinct cultivar of *Hibiscus rosa-sinensis* named 'Lanouachita' and will be referred to hereafter by its cultivar name, 'Lanouachita'. 'Lanouachita' is a new cultivar of tropical *hibiscus* grown for use as a landscape and container plant.

The new cultivar was developed through an ongoing breeding program conducted by the Inventor in Malause, France. The objectives of the breeding program are to develop new cultivars of *Hibiscus* that exhibit brightly colored flowers, self-branching, high flower bud counts, and compact plant habits.

'Lanouachita' arose from a cross made by the Inventor in July of 2009 between unnamed plants of *Hibiscus rosa-sinensis* from the breeding program, reference no. si Rio Clara Orange (not patented), as the female parent and no. si 078-5 (not patented), as the male parent. 'Lanouachita' was selected as a single unique plant from the resulting seedlings in September of 2013.

Asexual propagation of the new cultivar was first accomplished by stem cuttings in Malause, France in June of 2012 by the Inventor. Asexual propagation by stem cuttings has determined that the characteristics of the new cultivar are stable and are reproduced true to type in successive generations.

SUMMARY OF THE INVENTION

The following traits have been repeatedly observed and represent the characteristics the new cultivar. These attributes in combination distinguish 'Lanouachita' as a new and distinct cultivar of *Hibiscus.*

1. 'Lanouachita' exhibits flowers that are mottled tangerine orange in color with pink highlights and center.

2. 'Lanouachita' exhibits a floriferous habit with flowers that last for 2 to 3 days.
3. 'Lanouachita' exhibits an early blooming and freely flowering habit.
4. 'Lanouachita' exhibits a moderately upright, compact and self-branching plant habit.
5. 'Lanouachita' exhibits foliage that is resistant to pathogens common to *Hibiscus*, including *Pseudomonas* sp., *Phythium* sp., and *Phytophthora* sp.

The female parent of 'Lanouachita' differs from 'Lanouachita' in having flowers that are orange in color but last for a single day. The male parent of 'Lanouachita' differs from 'Lanouachita' in having flowers that are red in color and in having a less branched and much less compact plant habit. 'Lanouachita' can be most closely compared to the *Hibiscus* cultivars 'Satsuma' (not patented) and 'Sweet Potato' (not patented). 'Satsuma' is similar to 'Lanouachita' in having flowers that are similar in color and in being floriferous. 'Satsuma' differs from 'Lanouachita' in having a center (eye) that is yellow in color, leaves that are deeply crenated and in having a less compact plant habit. 'Sweet Potato' is similar to 'Lanouachita' in having a similar flower color and a moderately upright growth habit. 'Sweet Potato' differs from 'Lanouachita' in having flowers that are solid orange in color and heavily ruffled and in having a more upright plant habit.

BRIEF DESCRIPTION OF THE DRAWINGS

The accompanying colored photographs illustrate the overall appearance and distinct characteristics of the new *Hibiscus*. The photographs were taken of a 18 month-old plant of 'Lanouachita' as grown in a two-gallon container in Grand Saline, Tex.

The photograph in FIG. 1 provides a side view of 'Lanouachita' in bloom.

Figure 1:
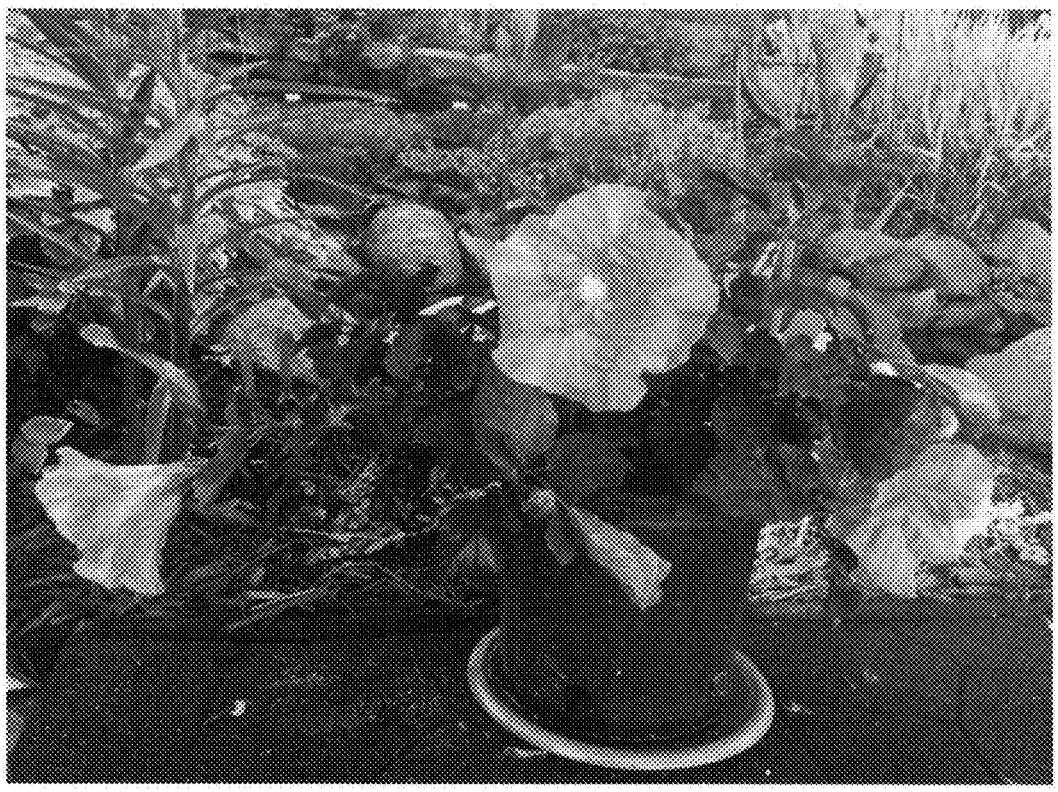
Figure 2:
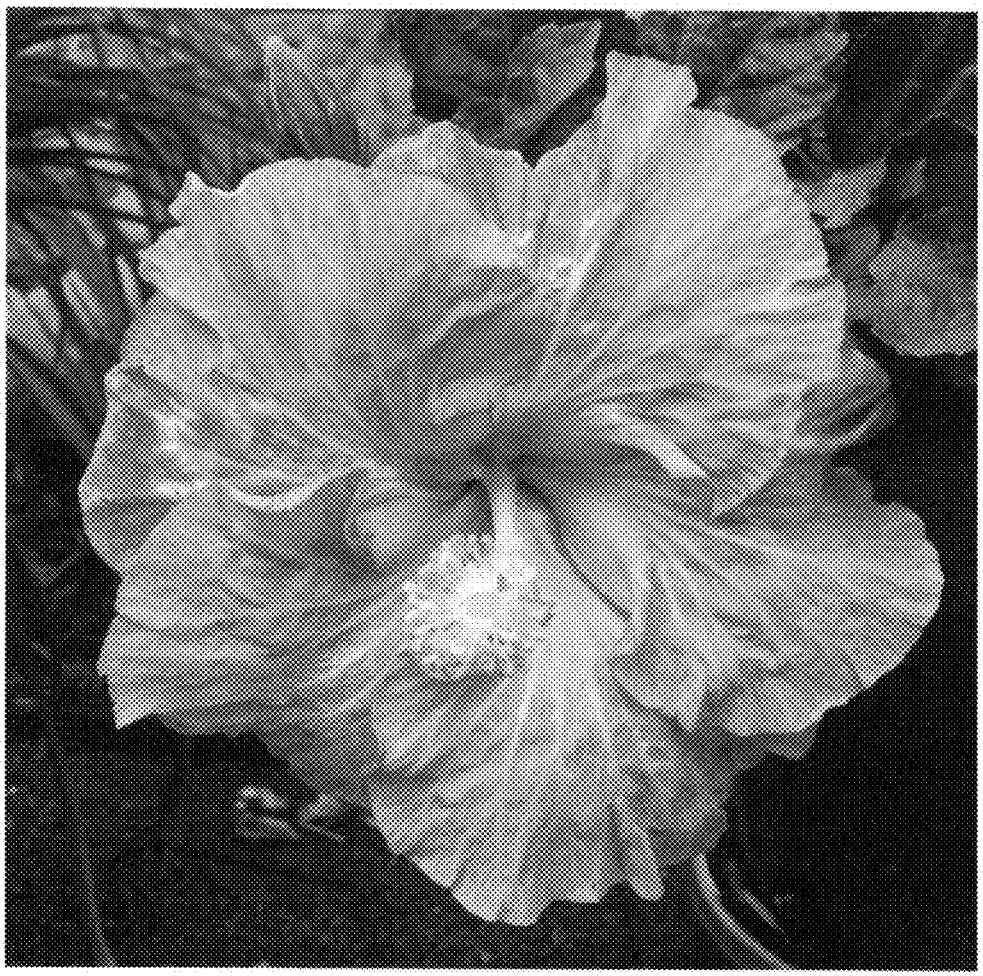

The photograph in FIG. 2 provides a close-up view of a flower of 'Lanouachita'.

The colors in the photographs are as close as possible with the photographic and printing technology utilized and the color values cited in the Detailed Botanical Description accurately describe the colors of the new *Hibiscus*.

DETAILED BOTANICAL DESCRIPTION OF THE PLANT

The following is a detailed description of 18 month-old plants of the new cultivar as grown in one-gallon containers in a greenhouse in Grand Saline, Tex. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General characteristics:

*Blooming period*.—Continuously producing in warm temperatures 55° F. to 90° F.

*Plant type*.—Tropical evergreen shrub.

*Plant habit*.—Moderately upright, compact and self-branching plant habit.

*Height and spread*.—An average of 32 cm in height and 52 cm in spread as grown in a one gallon container and reaches an average of 2.7 m in height and 2.1 m in spread when mature in the landscape.

*Hardiness*.—Tropical; at least in U.S.D.A. Zones 9 to 10.

*Diseases*.—Resistance to pathogens common to *Hibiscus*, including *Pseudomonas* sp., *Phythium* sp., and *Phytophthora* sp.

*Root description*.—Fibrous roots, 161A in color.

*Propagation*.—Stem cuttings.

*Root development*.—Roots initiate in about 56 days and develop as a young plant in about 6 months.

*Growth rate*.—Moderately vigorous.

Stem description:

*Shape*.—Slightly oval.

*Stem color*.—New growth; 146A, mature wood; 199D with striations of 197A.

*Stem size*.—An average of 22 cm in length and 5 mm in width.

*Stem surface*.—New growth; sparsely pubescent, mature wood; finely striated.

*Stem aspect*.—Held in multiple angles.

*Stem strength*.—Strong.

*Branching*.—An average of 12 lateral branches in a two-gallon container.

*Internode*.—Average of 2 cm (shorter near apex: average of 1 cm).

*Stipules*.—1 to 2 per upper leaf node, linear to narrowly lanceolate in shape, an average of 9 mm in length and 1 mm in width, glabrous surface, acuminate apex, truncate base, 144A in color.

Foliage description:

*Leaf shape*.—Ovate.

*Leaf division*.—Simple.

*Leaf base*.—Rounded.

*Leaf apex*.—Acute.

*Leaf venation*.—Pinnate, 137C on upper surface and 146B on lower surface.

*Leaf margins*.—Serrate and slightly wavy, tips of serration have a small mucronate tip.

*Leaf attachment*.—Petiolate.

*Leaf arrangement*.—Alternate.

*Leaf orientation*.—Slightly upward to horizontal to slightly downward to petiole.

*Leaf aspect*.—Primarily flat with slightly wavy margins.

*Leaf surface*.—Upper surface glabrous and satiny, lower surface very finely puberulent and slightly satiny.

*Leaf color*.—Young leaves upper surface; a color between 144A and 137A, mature leaves upper surface; 137A, young and mature leaves lower surface; a color between 144A and 137B.

*Leaf size*.—An average of 7 cm in length and 6 cm in width when mature.

*Leaf quantity*.—An average of 14 leaves per stem 18 cm in length.

*Petioles*.—An average of 2.0 cm in length and 2.5 mm in diameter, 138A in color, finely pubescent surface and flattened on upper surface.

Flower description:

*Inflorescence type*.—Flowers are solitary from upper leaf axils.

*Lastingness of flowers*.—An average of 2 to 3 days, self cleaning.

*Flower size*.—An average of 11 cm in depth and 14 cm in diameter (including calyx).

*Flower fragrance*.—None.

*Flower shape*.—Rotate.

*Flower number*.—Average of 7, up to 9 per lateral stem.

*Flower aspect*.—Outward to slightly upright.

*Flower bud*.—Elliptic in shape, an average of 5.5 cm in length and 3 cm in width, a blend of 10B and 22A and 34B in color with sepal portion 144A, glabrous surface.

*Petals*.—5, 5% fused, 10% overlapping, oblanceolate in shape, an average of 8 cm in length and 8 cm in width, slightly serrate and wavy margins, rounded apex, base is cuneate slightly oblique and adnate to base of style re-curved, lower surface is glossy, upper surface; satiny and waxy near the base (throat), color of upper surface when opening; a blend of 16D and 16A and flushes of 24A on the tips, 155B at the base (throat) with a spot of 61B, color upper surface fully open; a blend of 21A and 33A, veins 12D, base to mid-section a blend of NN155A and 49A, margins at base are flushed with 53B, color lower surface when opening; a blend of 11A and 21C, flushed with 35A on the outer tips, 155A at the base (throat) with a spot of 61B, color lower surface when fully open; a blend of 44A, 31A and N34A, veins 22C.

*Calyx*.—Campanulate in shape, average of 4 cm in length and 3 cm in diameter.

*Epicalyx*.—Comprised of 6 bracts held upright surrounding sepals, lanceolate in shape, apiculate apex, truncate base, average of 1.5 cm in length and 3 mm in width, color of both surfaces is 144A, both surfaces are glabrous and dull.

*Sepals*.—5, base 50% fused, an average of 1.5 cm in length and 1 cm in width, color of both surfaces is 144A, outer surface is puberulent and inner surface is glossy, acute apex, truncate base.

*Peduncles*.—An average of 4 cm in length and 3 mm in diameter, strong, average angle upright to outward, 143A, glabrous and glossy surface.

*Pedicels*.—Not present, flowers are solitary from terminal leaf axils.

*Receptacle*.—1 cm in diameter, 145A and 146A in color, glabrous and glossy surface.

Reproductive organs:

*Gynoecium*.—Pistil; 1, 7.5 cm in length, stigmas; 5, oblong in shape, 4 mm in diameter, surface covered with short fuzzy hairs, color when opening 11A, color when fully open 14A, style arms; 4 mm in length, 11C in color, surface is glabrous, style; average of 5 cm in length and 0.5 mm in width, smooth and glossy surface, color when opening 11C, color when fully open 8D, ovary; orbicular in shape with round apex, 5 mm in length and width, 2D in color.

*Androecium*.—Stamens; average of 50, stamens are clustered and implanted into upper portion of style, anthers; dorsifixed in shape, 2 mm in diameter, 1 mm in depth, color when opening and fully open 22B, filament; 7 mm in length, color when opening 11D, color when fully open 38A, pollen; moderate in quantity and 21A in color.

*Fruit/seeds*.—None observed to date.

It is claimed:

1. A new and distinct cultivar of *Hibiscus* plant named 'Lanouachita' as herein illustrated and described.

* * * * *